| United States Patent [19] | [11] Patent Number: 4,751,144 |
| Saito et al. | [45] Date of Patent: Jun. 14, 1988 |

[54] DENTURE BASE MADE OF THERMOPLASTIC RESIN

[75] Inventors: Teruo Saito, Shiga; Hiroshi Ishida, Hyogo; Tatsuo Goto, Niigata, all of Japan

[73] Assignee: Sumitomo Chemical Company, Ltd., Osaka, Japan

[21] Appl. No.: 93,103

[22] Filed: Sep. 1, 1987

Related U.S. Application Data

[63] Continuation of Ser. No. 874,490, Jun. 16, 1986, abandoned.

[30] Foreign Application Priority Data

Jun. 24, 1985 [JP]  Japan ................................ 60-138808

[51] Int. Cl.⁴ ............................................. B32B 27/36
[52] U.S. Cl. .................................... 428/412; 525/437; 525/439; 525/462; 525/535; 428/480; 433/199.1

[58] Field of Search ............... 525/437, 439, 462, 535; 428/412, 411.1, 480

[56] References Cited

U.S. PATENT DOCUMENTS

| 4,358,569 | 11/1982 | Quinn et al. | 525/439 |
| 4,460,736 | 7/1984 | Froix et al. | 524/539 |
| 4,503,168 | 3/1985 | Hartsing, Jr. | 523/100 |

*Primary Examiner*—Theodore E. Pertilla
*Attorney, Agent, or Firm*—Ladas & Parry

[57] ABSTRACT

A denture-base made of a thermoplastic resin compound which comprises polysulfone resins (A) and a resin (B) selected from the group consisting of polycarbonates, polyester carbonates, aromatic polyester copolymers and their mixtures, is excellent in mechanical properties and compatibility with acrylic resins, firmly implants artificial dentures of acrylic resin, and is readily repaired by use of repair materials of acrylic resin.

9 Claims, No Drawings

DENTURE BASE MADE OF THERMOPLASTIC RESIN

This is a continuation of co-pending application Ser. No. 874,490 filed on Jun. 16, 1986 now abandoned.

BACKGROUND OF THE INVENTION

This invention relates to a denture-base made of a compound comprising thermoplastic resins having different properties, which is excellent in appearance, mechanical properties, repairability etc.

Denture-bases have been produced for many years from acrylic resins by compression molding method wherein their polymers and monomers are polymerized by heat. An advantage of the acrylic resin denture-bases is that they can be readily repaired by use of acrylic polymer powders and acrylic monomer liquid as repair materials.

The acrylic resin denture-bases thus produced by thermal polymerization are, however, weak in strength so that thin portions therof are often broken by occlusal forces. In addition, the said denture-bases might be poisonous so as to cause allergy due to effluence of residual monomers resulting from incompletion in thermal polymerization reaction.

Denture-bases made of thermoplastic resins such as polysulfone have also been proposed and practically used to eliminate the above drawbacks of acrylic resins, which are produced by injection or compression molding in gypsum molds.

The denture-bases of thermoplastic resins such as polysulfone are superior in strength to those made of acrylic resins, because the thermoplastic resins such as polysulfone are excellent in impact resistance compared with conventional acrylic resins. However, the said denture-bases are difficult to repair and cannot endure a long-term use because they tend to have stress-cracking in contact with instantaneous polymerizing resins composed of acrylic monomers, particularly methyl methacrylate which is most commonly used for repairing acrylic resin denture-bases.

The application to denture-bases of polyester or polycarbonate resins such as polycarbonates, polyester carbonates, aromatic polyester copolymers and their mixtures, is under investigation. These resins are superior in compatibility with methyl methacrylate and have few stress-cracking in contact with methyl methacrylate, compared with the polysulfone resins as mentioned above. These resins, however, tend to have stress-cracking in contact with isobutyl methacrylate or nor-malbutyl methacrylate which is a component of relining resins or repair materials.

SUMMARY OF THE INVENTION

It is an object of the present invention to provide a denture-base made of thermoplastic resins which is excellent in mechanical properties and compatibility with acrylic monomers.

This object is accomplished by a denture-base made of a thermoplastic resin compound comprising polysulfone resins (A) and a resin (B) selected from the group consisting of polycarbonates, polyester carbonates, aromatic polyester copolymers and their mixtures.

The inventive denture-base is excellent in adhesion to artificial dentures of acrylic resin. And it is possible to apply to the inventive denture-base various instantaneous polymerizing resins which have been used as repair resins or relining resins for acrylic resin denture-bases. This invention, therefore, contributes to make expanded the scope of the application of thermoplastic resin denture-bases with various advantages.

DETAILED DESCRIPTION OF THE INVENTION

The polysulfone resins used in this invention can be defined as polyarylene compounds having arylene units which are arranged orderly or not together with ether linkage and sulfone linkage. Examples of the said polysulfone resins are those having structures (1)–(16) as follows:

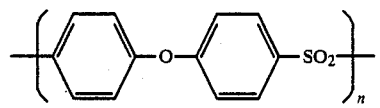

(1)

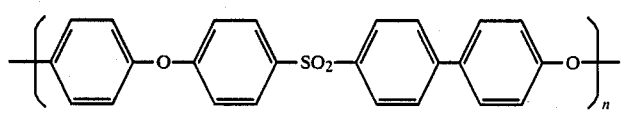

(2)

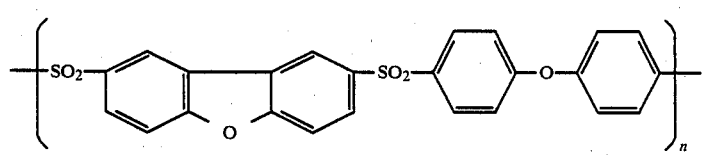

(3)

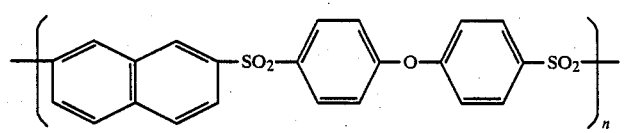

(4)

-continued
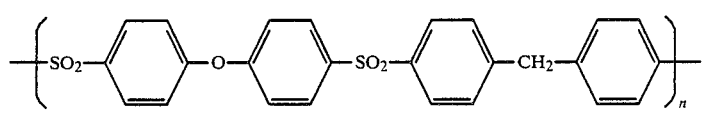 (5)
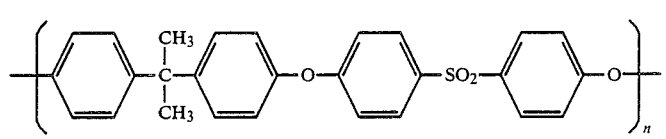 (6)
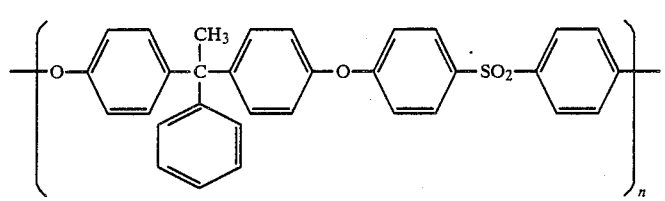 (7)
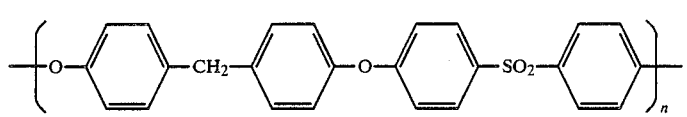 (8)
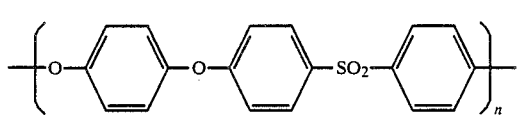 (9)
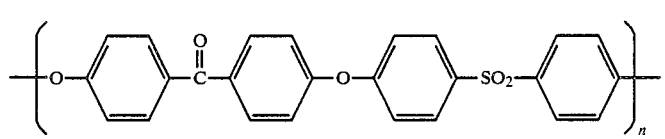 (10)
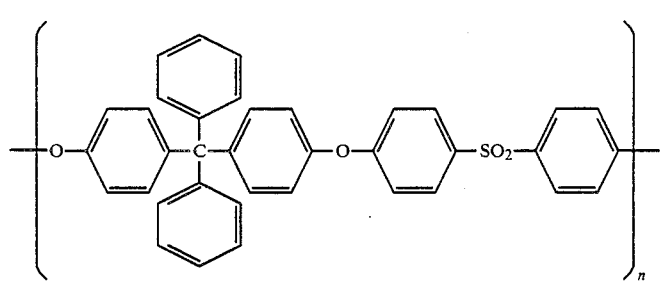 (11)
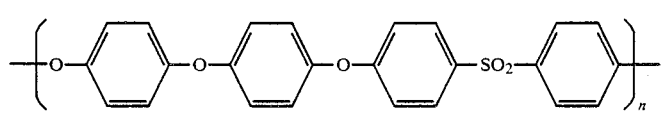 (12)
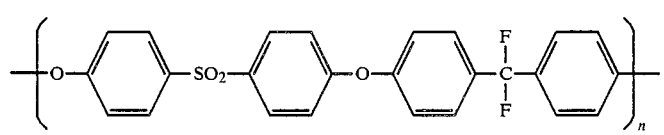 (13)
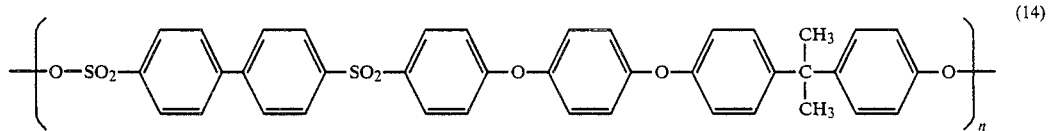 (14)

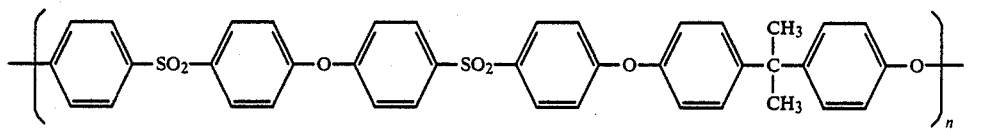

(15)

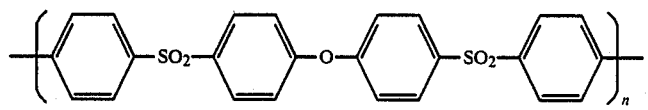

(16)

Particularly preferred are the polysulfone resins having the structures (1), (2) and/or (6) since they are well-balanced in physical properties and processability. Polysulfone resin of the type having the structure (1) is commercially available from ICI as Victrex ® polyethersulfone. Polysulfone resin of the type having the structure (6) is also commercially available from UCC as Udel ® polysulfone. The polysulfone resins preferably have a reduced viscosity of not less than 0.3 and not more than 0.6 as measured at 25° C. in a dimethylformamide solution containing 1 gram of the polymer in 100 ml of the solution, because the polysulfone resins having such a reduced viscosity are superior in physical properties such as heat resistance, strength and stiffness, and shapability.

The polycarbonates used in this invention are 4,4-dioxydiarylalkane polycarbonates which can be derived from 4,4-dioxydiphenylalkanes such as bis(4-hydroxyphenyl)methane, bis(4-hydroxyphenyl)ethane, 2,2-bis(4-hydroxyphenyl)propane, bis(4-hydroxy-3,5-dichlorophenyl)methane, 2,2-bis(4-hydroxy-3,5-dimethylphenyl)propane, bis(4-hydroxyphenyl)phenylmethane and phosgene or diphenylcarbonates. These polycarbonates are produced by various known methods such as melt polymerization, interfacial polymerization, etc.

The polyester carbonates used in this invention are obtained from component A of aromatic dicarboxylic acids and/or their functional derivatives, component B of aromatic dihydroxy compounds and/or their functional derivatives, and component C of diaryl carbonates or phosgene.

Examples of the component A are terephthalic acid, isophthalic acid, methyl terephthalic acid, methyl isophthalic acid, diphenyletherdicarboxylic acid, diphenoxyethanedicarboxylic acid, naphthalenedicarboxylic acid, and their ester-forming derivatives such as lower alkyl esters, phenyl esters, acid halides etc.

Examples of the component B are hydroquinone, resorcine, 2,2-bis(4-hydroxyphenyl)propane (bisphenol A), 4,4'-dihydroxydiphenyl, 1,1-bis(4-hydroxyphenyl)-cyclohexane, 1,1-bis(4-hydroxyphenyl)ethane, bis-(4-hydroxyphenyl)methane, 2,2-bis(4-hydroxy-3,5-dibromophenyl)propane, 4,4'-dihydroxydiphenylsulfone, 1,2-bis(4-hydroxyphenyl)ethane and their ester-forming derivatives. The component B may be composed of one or more of the compounds listed above. Of the compounds, particularly preferred are bisphenol A.

Examples of the diaryl carbonates of the component C are diphenylcarbonate, dicresylcarbonate, di-β-naphthylcarbonate, bis(2-chlorophenyl)carbonate.

The polyester carbonate particularly preferred is a combination of terephthalic acid or diphenyl terephthalate ester, bisphenol A and diphenylcarbonate.

The said polyester carbonates preferably have the ratio of ester to carbonate of 1/9–9/1 and the ultimate viscosity of 0.4-1.1 as measured at 25° C. in a chloroform solvent. If the ultimate viscosity is over 1.1, shapability deteriorates. If the ultimate viscosity is below 0.4, mechanical properties are insufficient.

The polyester carbonates used in this invention can be produced from the above three components A, B and C by any methods such as bulk polycondensation, solution polycondensation, interfacial polycondensation, etc.

The aromatic polyester copolymers used in this invention are obtained by copolymerization of a mixture of terephthalic acid and isophthalic acid or their functional derivatives (having 9/1 to 1/9 of the molar ratio of terephthalic acid groups to isophthalic acid groups), and 2,2-bis(4'-hydroxyphenyl)propane (hereinafter referred to bisphenol A).

These aromatic polyester copolymers can be produced by known methods, for example, interfacial copolymerization (W. M. Eareckson. J. Poly. Sci. XL 339, 1959, Japanese Patent Examined Publication No.40-1959) wherein aromatic dicarboxylic chlorides solved in a water-insoluble organic solvent are blended and reacted with bisphenols solved in an alkali solution, solution polymerization (A. Conix. Ind. Eng. Chem. 51 147, 1959, Japanese Patent Examined Publication No. 37-5599) wherein aromatic dicarboxylic chlorides and bisphenols are reacted in an organic solvent, and melt polymerization (Japanese Patent Examined Publication No. 38-15247) wherein aromatic dicarboxylic acids and bisphenols are heated in the presence of acetic anhydride.

The mixtures of resin (B) used in this invention may consist of either two or three of polycarbonates, polyester carbonates and aromatic polyester copolymers which have compatibility with each other. Of the above mixtures, particularly preferable is the mixture consisting of 70-5% by weight of polycarbonates and 30-95% by weight of aromatic polyester copolymers because the mixture is excellent and well-balanced in transparence, strength, stiffness, resistance to methyl methacrylate and shapability and is superior in surface hardness and resistance to abrasion by tooth brushes.

The method of preparing the compound used in this invention from resin (A) and resin (B) is not critical.

Examples of compression molding for the inventive denture-base are a method comprising layering a plurarity of plate-like molds made of resin (A) and resin (B) approximating the size of an alveolar ridge, heating the molds to make them soften and then closing the top and bottom flasks to perform compression molding, and a method comprising heating a pre-formed two-layer or sandwitch-like mold having layers of resin (A) and resin (B) to make it soften and then perform compression molding. An example of injection molding for the inventive denture-base is a method comprising injecting resin (A) and resin (B) which have been melted in different cylinders into a sealed mold cavity simultaneously or alternately. Preferably employed is the method of compression molding using a plurarity of multi-layer molds made of resin (A) and resin (B), since the resultant denture-base is superior in resistance to acrylic monomers because of its multi-layer structure of resin (A) and resin (B).

Plate-like molds prepared from a blend or a mixture of granules or particulates of resin (A) and resin (B) in an extruder or a mixer such as a banbary mixer are not suitable to materials for the inventive denture-base. If such plate-like molds are employed, the resultant denture-base does not have gingiva-like appearance but has pearlescence or opacity due to scattering of visible radiations caused by the difference in refractive index between resin (A) and resin (B).

The state in the compound of this invention should not be a mixture or blend as mentioned above, but be a compound having integrated layers part of which may be blends of resin (A) and resin (B), since the latter state prevents scattering visible radiations, maintains transparency and has excellent bonding between resin (A) and resin (B) and other performances suitable to denture-bases.

The outer layer of the compound thus produced may be of resin (A) or resin (B), preferably, of resin (B), since resin (B) is excellent in compatibility with methyl methacrylate commonly used as repair resin and in bonding with artificial acrylic resin dentures compared with resin (A).

The compound of this invention preferably consists of 10–90% by weight of resin (A) and 90–10% by weight of resin (B), more preferably, 20–80% by weight of resin (A) and 80–20% by weight of resin (B) since the denture-bases with such proportion have excellent resistance to methyl methacrylate, isobutyl methacrylate, normalbutyl methacrylate etc. used as repair resins or relining resins and is excellent in properties such as appearance, strength, stiffness, etc.

Within the scope of this invention, one or more of ordinary additives such as antioxidants, heat stabilizers, ultraviolet absorbers, lubricants, mold release agents, dyes, pigments, colorants may be added to resin (A) and resin (B).

In order to more specifically explain this invention, specific examples are set forth hereinafter. However, it is noted that this invention is not limited by the specific examples set forth below.

EXAMPLE 1

Top and bottom flasks in which wax master models of denture-base having artificial teeth of acrylic resin (anterior and posterior teeth of acrylic resin manufactured by GC) were embedded respectively were heated to soften the wax and melt it away. Thereafter, a U-shaped mold (approxmating the size of an alveolar ridge and having the thickness of 3 mm) composed of a blend having the ratio of 7:3 of aromatic polyester copolymer colored in gingiva color (which was obtained by interfacial polymerization from terephthalic dichloride and isophthalic dichloride in the proportion of 1:1 in a methylene chloride solution and bisphenol A in an alkalic solution, and had 0.62 of logarithmic viscosity as measured in a phenol/tetrachloroethane (of 6:4 by weight) solvent) to polycarbonate (S 2000 manufactured by Mitsubishi Gas Chemical Co., Inc.) was placed on a gypsum mold in the bottom flask and was softened by blowing air heated at 340° C.

After the above mold softened well, a U-shaped mold colored in gingiva color consisting of polyether sulfone (Victrex® PES 4100G manufactured by ICI) was placed onto the above softening blend of polyester copolymer and polycarbonate and was softened by blowing air heated at 340° C. Thereafter, a U-shaped mold consisting of a blend having aromatic polyester copolymer and polycarbonate was placed onto the above mold of polyether sulfone and was heated to soften.

And other molds of polyether sulfone and of a blend having aromatic polyester copolymer and polycarbonate were respectively placed thereon and heated to soften in the gypsum mold in the bottom flask as mentioned above. After the five layers thus produced softened well, the flasks were closed to perform compression molding and then were left cooling in air. After having been cooled, the top flask was separated from the bottom flask to take out a denture-base product. The denture-base rigidly embedded the artificial teeth and had no sink marks and a size which corresponds faithfully to the wax master model.

The denture-base was made in contact with an repair resin for conventional acrylic denture-bases, that is, an instantaneous polymerizing resin (GC Revaron®) primarily based on methyl methacrylate by building up it onto the denture-base using ordinary brushing method. The denture-base was found to have no accident such as cracks.

Furthermore, a palatal portion of the denture-base was made in contact with a relining resin for acrylic resin denture-bases, that is, an instantaneous polymerizing resin (KooLiner® manufactured by Coe Co.) primarily based on isobutyl methacrylate by building up it thereon. The denture-base was found to have no changes such as cracks.

It is, therefore, observed that both of the above instantaneous polymerizing resins can be applied to the said denture-base.

COMPARATIVE EXAMPLE 1

A denture-base was obtained by the same compression molding as in Example 1 except that only U-shaped molds of polyether sulfone were employed in place of the U-shaped molds of polyether sulfone and of the blend having aromatic polyester copolyer and polycarbonate. However, artificial teeth were disengaged from the denture-base only by faintly pushing them.

The said denture-base made of polyether sulfone was made in contact with an instantaneous polymerizing resin (GC Revaron®) primarily based on methyl methacrylate by building up it thereon using a brush as in Example 1. The denture-base was found to have cracks in the portions such as those adjacent to artificial teeth where many residual strains occur.

In contact with an instantaneous polymerizing resin (KooLiner®) primarily based on isobutyl methacrylate, the denture-base was found to have no appreciable cracks.

COMPARATIVE EXAMPLE 2

A denture-base was obtained by the same compression molding as in Example 1 except that only U-shaped molds composed of a blend having aromatic polyester and polycarbonate in the proportion of 7:3 were employed in place of the U-shaped molds of polyether sulfone and of the blend having aromatic polyester and polycarbonate. The resultant denture-base rigidly embedded artificial teeth and was excellent in appearance.

The denture-base was made in contact with the two types of instantaneous polymerizing resins as employed in Example 1. In contact with the instantaneous polymerizing resin primarily based on methyl methacrylate, the denture-base was found to have no cracks. In contact with that primarily based on isobutyl methacrylate, it was found to have cracks which made it unsuitable for practical use.

EXAMPLE 2

A mold having the same U-shape as in Example 1 was obtained from polysulfone pellets (Udel ® P1700 manufactured by UCC) and aromatic polyester copolymer pellets colored in gingiva color by use of a mixing injecting molding machines FSD-150 manufactured by Nissei Jushi. The proportion of polysulfone to aromatic polyester copolymer of the said mold was about 1:1. Since the molder has two cylinders from which each resin is injected into the die, the resultant mold was a compound which was not a complete mixture, but had integrated layers each resin.

A denture-base was obtained by the same compression molding as in Example 1 from the compounded U-shaped mold. The said denture-base had no problems such as sink marks.

In contact with the same instantaneous resin (GC Revaron ®) primarily based on methyl methacrylate as employed in Example 1 and a relining resin (Parabase ® manufactured by Kulzer Co.) composed of methyl methacrylate and about 30% of normalbutyl methacrylate, the denture-base was found to have no cracks and to be repaired well.

COMPARATIVE EXAMPLE 3

A denture-base was obtained by the same procedure as in Example 2 except that a U-shaped mold was prepared from only polysulfone in place of the compounded U-shaped mold in Example 2.

In contact with GC Revaron ®, the resultant denture-base was found to have cracks.

COMPARATIVE EXAMPLE 4

A denture-base was obtained by the same procedure as in Example 2 except that a U-shaped mold was prepared only from aromatic polyester in place of the compounded U-shaped mold in Example 2.

In contact with Parabase ®, the resultant denture-base was found to have cracks.

EXAMPLE 3

A denture-base was obtained by the same procedure as in Example 2 except that polyester carbonate (which was prepared by bulk polycondensation from terephthalic acid, bisphenol A and diphenylcarbonate, had the following formula as a basic structure:

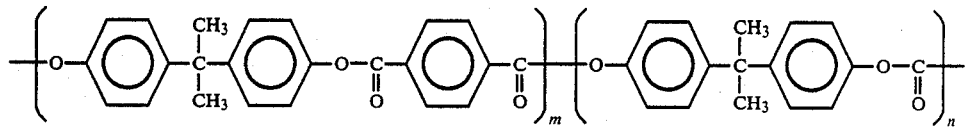

and had the ultimate viscosity of 0.655 as measured in chloroform solvent at 25° C., the m/n being 51/49) was employed in place of the aromatic polyester copolymer. The resultant denture-base had no problems such as sink marks.

In contact with an instantaneous resin (GC Revaron ®) primarily based on methyl methacrylate and a relining resin (Parabase ®) of methyl methacrylate and about 30% of normalbutyl methacrylate, the denture-base was found to have no cracks and to be repaired well.

COMPARATIVE EXAMPLE 5

A denture-base was obtained by the same procedure as in Example 3 except that a U-shaped mold composed only of polyester carbonate was employed in place of the compounded U-shaped mold in Example 3.

In contact with Parabase ®, the resultant denture-base was found to have cracks.

We claim:

1. A denture base comprising a alternatively layered structure of thermoplastic resins, of a polysulfone resin (A) and a resin (B) selected from the group consisting of polycarbonates, polyester carbonates, aromatic polyester copolymers and mixtures thereof.

2. A denture base, as in claim 1, wherein the outer layer of said denture base comprises resin (B).

3. A denture base, as in claim 1, wherein said base comprises 10-90% by weight of resin (A) and 90-10% by weight of resin (B).

4. A denture base, as in claim 3, wherein said denture base comprises 20-80% by weight of resin (A) and 80-20% by weight of resin (B).

5. A denture base, as in claim 3, wherein said polysulfone resin has a reduced viscosity of 0.3-0.6.

6. A denture base according to claim 1 wherein said resin (B) is a mixture consisting of 70-5% by weight of polycarbonates and 30-95% by weight of aromatic polyester copolymers.

7. A denture base according to claim 1 wherein said polycarbonates are 4,4-dioxydiarylalkane polycarbonates which can be derived from 4,4-dioxydiphenylalkane and phosgene or diphenylcarbonate.

8. A denture base according to claim 1 wherein said polyester carbonates are those obtained from terephthalic acid or diphenyl terephthalate ester, bisphenol A and diphenylcarbonate.

9. A denture base, as in claim 1, further comprising one or more of the group selected from anti-oxidants, heat stabilizers, mold release agents, dyes or pigments.

* * * * *